United States Patent [19]

Perry

[11] Patent Number: 5,166,613
[45] Date of Patent: Nov. 24, 1992

[54] METHOD AND APPARATUS FOR MAPPING STRESS WITHIN FERRROMAGNETIC MATERIALS BY ANALYZING BARKHAUSEN NOISE FORMED BY THE INTRODUCTION OF MAGNETIC FIELDS

[75] Inventor: William D. Perry, San Antonio, Tex.

[73] Assignee: Southwest Research Institute, San Antonio, Tex.

[21] Appl. No.: 609,837

[22] Filed: Nov. 6, 1990

[51] Int. Cl.$^5$ .................. G01B 7/24; G01N 27/80; G01R 33/12
[52] U.S. Cl. .................. 324/209; 324/232; 73/862.69; 73/779
[58] Field of Search ............. 324/209, 226, 239, 240, 324/241, 242, 243, 232; 73/779, 862.69, 1 B, 1 C, 801

[56] References Cited

U.S. PATENT DOCUMENTS

| | | |
|---|---|---|
| 1,958,079 | 5/1934 | Billstein . |
| 1,984,465 | 12/1934 | Dana . |
| 2,098,064 | 11/1937 | Pfaffenberger . |
| 2,103,224 | 12/1937 | Schweitzer . |
| 2,267,884 | 12/1941 | Zuschlag . |
| 2,398,488 | 4/1946 | Zuschlag . |
| 2,448,794 | 9/1948 | Goldsmith . |
| 2,660,704 | 11/1953 | Harmon . |
| 3,022,451 | 2/1962 | Chapman . |
| 3,427,872 | 2/1969 | Leep . |
| 3,737,764 | 6/1973 | Dufayet . |
| 3,783,370 | 1/1974 | Birdwell . |
| 3,875,502 | 4/1975 | Neumaier . |
| 4,146,837 | 3/1979 | Bashkirov ............. 324/255 |
| 4,188,577 | 2/1980 | Mhatre ............... 324/220 |
| 4,215,310 | 7/1980 | Schwerer ............. 324/225 |
| 4,352,065 | 9/1982 | Rogachev ............. 324/238 |
| 4,408,160 | 10/1983 | King et al. ........... 324/209 |
| 4,466,287 | 8/1984 | Repplinger et al. .... 324/226 X |
| 4,497,209 | 2/1985 | Kwun et al. .......... 324/209 X |
| 4,599,563 | 7/1986 | Tiitto et al. ......... 324/209 X |
| 4,634,976 | 1/1987 | Tiitto ................. 324/209 X |
| 4,689,558 | 8/1987 | Ruuskanen et al. ..... 324/209 |
| 4,692,701 | 9/1987 | Dundas et al. ........ 324/209 X |
| 4,881,030 | 11/1989 | Stuecker et al. ...... 324/209 |
| 4,931,730 | 6/1990 | Olsen et al. ......... 324/209 |

OTHER PUBLICATIONS

Pasley, R., Barkhausen Effect—An Indication of Stress, Materials Evaluation, vol. 28, No. 7, Jul. 1970, pp. 157-161.

Primary Examiner—Gerard R. Strecker
Assistant Examiner—Warren S. Edmonds
Attorney, Agent, or Firm—Gunn, Lee & Miller

[57] ABSTRACT

A system for identifying and measuring stress at specific locations within a ferromagnetic material by the production and detection of Barkhausen noise during magnetization of the material. The method involves introducing into the material a time varying magnetic field component and a spatially-varying magnetic field component that in combination create a singular zero magnetic flux element within the material that "sweeps" from one position within the material to another and back. By time-gating the detected acoustic Barkhausen signal that results as this zero flux element moves within the material, the signal is isolated as having been generated at a specific depth within the specimen. Since the level of Barkhausen noise varies with stress, a tomographic mapping of stress is obtained for the interior of the ferromagnetic specimen. Through the use of a computer, a three dimensional map of stress in the ferromagnetic material is obtained.

9 Claims, 6 Drawing Sheets

APPLIED MAGNETIC FIELD vs. TIME    HYSTERESIS LOOP
a. NO STATIC BIAS FIELD
$H_s = 0$
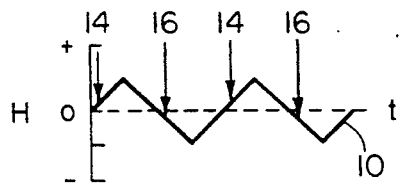 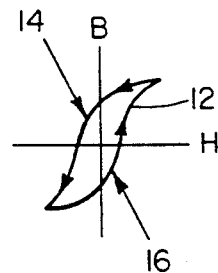
b. $H_s < 0$
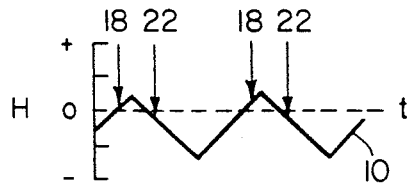 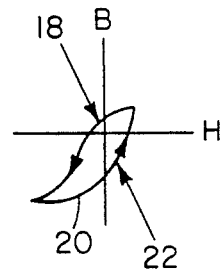
c. $H_s > 0$
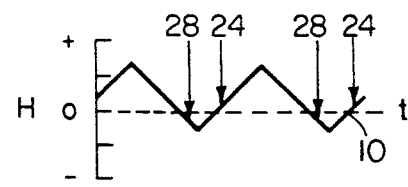 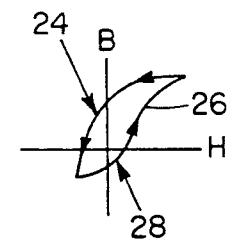
FIG. 1

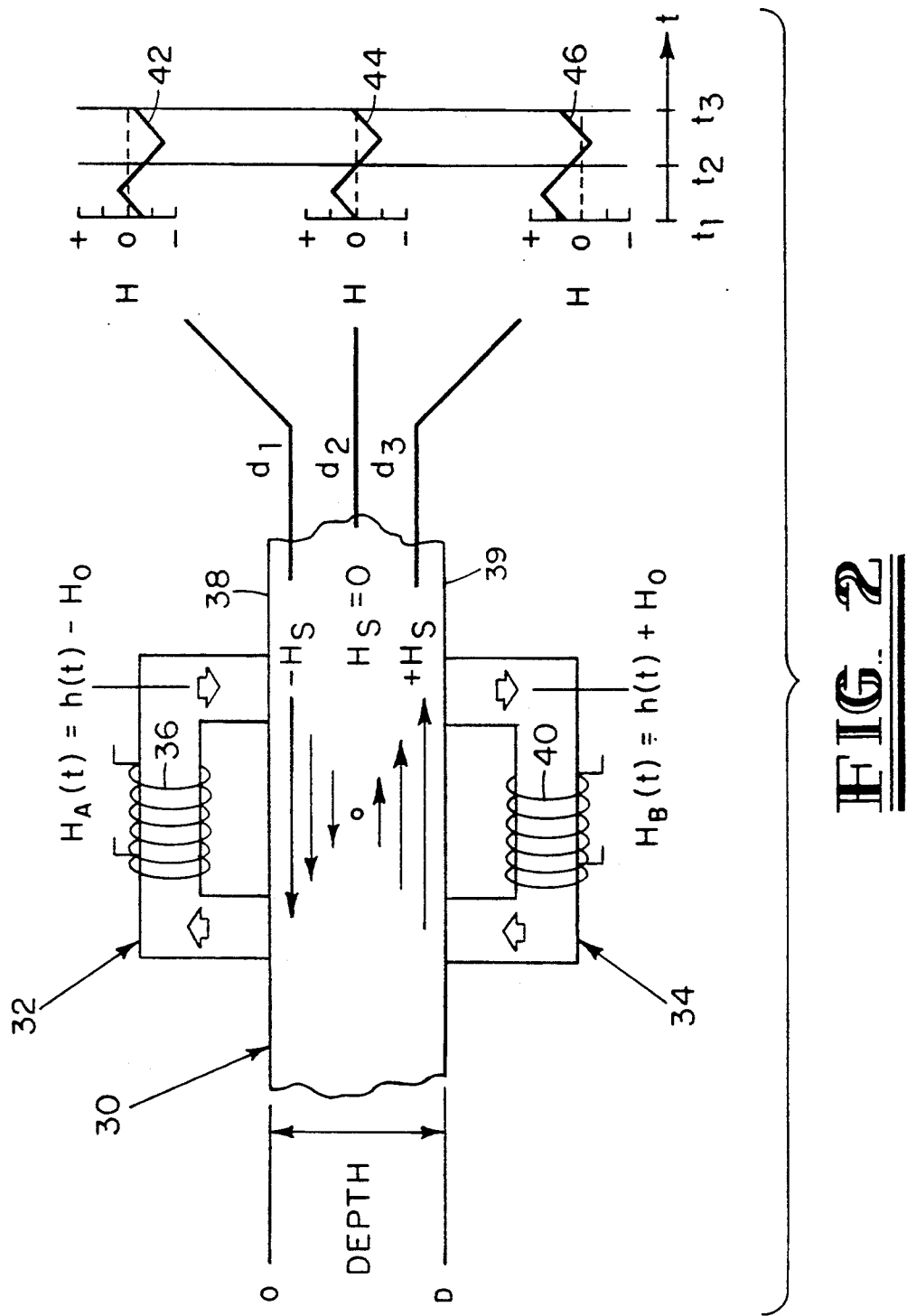

ମETHOD AND APPARATUS FOR MAPPING STRESS WITHIN FERRROMAGNETIC MATERIALS BY ANALYZING BARKHAUSEN NOISE FORMED BY THE INTRODUCTION OF MAGNETIC FIELDS

BACKGROUND OF THE INVENTION

The present invention relates to the use of Barkhausen noise to determine stress within the interior of a ferromagnetic specimen by creating both a cyclic and a spatially-varying bias magnetic fields within the specimen. By time-gating a detected Barkhausen noise signal, a tomographic map of stress within the ferromagnetic specimen can be produced.

The interior stress in many components are often of interest in determining whether the component can perform its function without failure. Non-destructive evaluation (NDE) methods for stress measurement include x-ray diffraction, ultrasonic bi-refringence, magnetically introduced ultrasonic velocity change, and Barkhausen noise. Barkhausen noise can be sensed either inductively or acoustically. The approaches used in the past, however, are limited either to measurement of stress at or near the surface, or measurement of the average bulk stress throughout a volume of material. The present invention shows a new approach which allows the internal stress to be determined at specific regions in the interior of the ferromagnetic material using acoustically detected Barkhausen noise.

The Barkhausen effect is caused by the discontinuance and irreversible motion of magnetic domain walls as a ferromagnetic material is magnetized. It is well known that the Barkhausen activity is influenced by the state of the mechanical stress in the material, and can be used to measure the residual or applied stress. The Barkhausen noise may be sensed as either a burst of voltage pulses introduced in the pick-up coil or as ultrasonic pulses detected by an acoustical transducer. The inductive detection method is limited to stress measurements in only the near surface region since the skin effect causes attenuation of the magnetic disturbances associated with the domain wall motion deeper in the interior of the material. The acoustical pulses originating in the interior of the material are not strongly attenuated with distance, and, therefore, the acoustical detection method offers the possibility of interior stress measurement.

The use of the Barkhausen effect to determine stress is explained in more detail in "Barkhausen Effect—An Indication of Stress," *Materials Evaluation*, Vol. 28, No. 7, July 1970, pages 157–61, which article was written by an employee of Southwest Research Institute, the assignee of the present invention. Also, U.S. Pat. No. 3,783,370 by Birdwell shows a feedback system for amplifying the Barkhausen signal when doing an NDE test. Neither of these references show the use of cyclic and spatially-varying bias magnetic fields that produce a time-gated signal for determining the Barkhausen noise in a specific interior region of a ferromagnetic specimen. It is the measurement in the interior region that allows for the tomographic mapping of the stress throughout the specimen.

A basic discussion of Barkhausen theory and the basic method and apparatus for NDE investigation of a ferromagnetic specimen by means of measuring Barkhausen noise can be found in U.S. Pat. No. 3,427,872 entitled "Method and System for Investigating the Stress Condition of Magnetic Materials" issued Feb. 18, 1969, to R. W. Leep and Richard L. Pasley, which is hereby incorporated by reference.

The Barkhausen noise is typically generated by applying a cyclic magnetic field to the material; however, this causes acoustic Barkhausen noise to be produced at the same time throughout the entire magnetized region of the material. Therefore, it is not possible to distinguish the noise from specific regions. The present invention describes a new approach which uses a combination of cyclic and spatially-varying magnetic fields to produce Barkhausen noise from specific regions in the specimen at specific times in the magnetization cycle. By time-gating the acoustic Barkhausen signal, stress can be measured in specific regions in the interior of the specimen by measuring the gated signal amplitude. The approach offers the possibility of a tomographic measurement of stress distribution throughout the interior of a specimen.

SUMMARY OF THE INVENTION

An object of the present invention is to provide a non-destructive evaluation of a ferromagnetic specimen to determine stress in the interior regions of the specimen.

It is another object of the present invention to utilize Barkhausen noise to determine the stress distribution in the interior of a ferromagnetic specimen.

It is yet another object of the present invention to utilize Barkhausen noise for non-destructive evaluation of a ferromagnetic specimen that uses a combination of both cyclic and spatially-varying bias magnetic fields for determining the Barkhausen noise and, hence, the stress in interior regions of the ferromagnetic specimen.

It is still another object of the present invention to do tomographic mapping of stress distribution in the interior region of a ferromagnetic specimen utilizing Barkhausen noise.

According to the principles of the present invention, a spatially-varying bias magnetic field is applied to a ferromagnetic specimen. Superimposed on the spatially-varying bias magnetic field is a cyclic-varying magnetic field. The combined magnetic fields causes each of the regions in the interior of the ferromagnetic specimen to produce Barkhausen noise as they cross the zero axis during the magnetization cycle. By time-gating the detection of the Barkhausen noise, the Barkhausen noise in a specific interior region of the ferromagnetic specimen is determined depending upon the field condition of the cyclic magnetic field. By measuring the Barkhausen noise at each specific interior region, a tomographic map can be provided. The stress in a specific region is determined from the signal amplitude as compared to the signal amplitude of a non-stressed specimen.

BRIEF DESCRIPTION OF THE DRAWINGS

FIG. 1 is a series of curves depicting the location of the maximum Barkhausen activity for applied cyclic magnetic field with different static bias magnetic fields where H is the magnetic intensity, B is the flux density, and t is time.

FIG. 2 is a schematic diagram of a configuration for producing Barkhausen noise at different times for different depths and showing idealized static bias field distribution $H_s$ and cyclic magnetic fields at three discrete depths.

FIG. 3b is the magnetic field distribution at various times for a magnetic field as illustrated in FIG. 3a.

DESCRIPTION OF THE PREFERRED EMBODIMENT

Figure 3A:
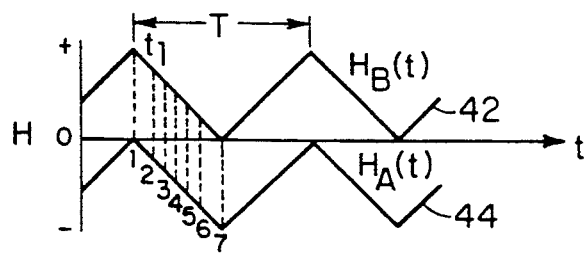
FIG. 3a is an illustrative plot of the magnetic field H versus time t for a specimen with the apparatus as depicted in FIG. 2.

Barkhausen noise is generated as a ferromagnetic material is exposed to a time varying magnetic field. Generally, the maximum Barkhausen activity occurs on the steep portion of the hysteresis curve, after the applied magnetic field crosses zero. Referring to FIG. 1, an applied cyclic magnetic field H has been illustrated with a triangle shaped wave form 10 plotted versus time t. In FIG. 1a, no static bias magnetic field is applied. Therefore, equal portions of the triangular shaped wave form 10 appear above and below the zero line for the magnetic field H. The static bias magnetic field is represented by the symbol $H_s$. A hysteresis loop curve 12 is illustrated for the wave form 10 with $H_s=0$. The hysteresis loop curve 12 is a plot of the magnetic field H versus the magnetic flux B. During the positive portion of the applied triangular shaped wave form 10 for the magnetic field, the time of the maximum Barkhausen activity is illustrated by the numeral 14. The same time applies for the hysteresis loop 12 and is also illustrated by the numeral 14 in the plot of the hysteresis loop 12.

Concerning the negative portion of the applied magnetic field H, the time of the maximum Barkhausen activity is illustrated by the reference numeral 16. Generally, the Barkhausen regions occur every half period of the magnetization cycle and are equally spaced with respect to time. However, the time at which the Barkhausen noise occurs can be shifted to any desired position during the cycle of magnetization by applying an additional static bias magnetic field $H_s$.

In FIG. 1b, a static bias magnetic field of $H_s$ less than zero is applied to move the triangular shaped wave form 10 in the negative direction. Now the maximum Barkhausen activity on the positive portion of a triangular shaped wave form 10 occurs at time 18 which is also illustrated in hysteresis loop curve 20. The time of the maximum Barkhausen activity for the negative portion of the triangular shaped wave form 10 is illustrated by the reference numeral 22, which also appears in the hysteresis loop curve 20. As illustrated in FIG. 1b, the static bias field $H_s$ shifts the zero crossing point of the applied magnetic field H. As a result, the time at which the Barkhausen noise occurs shifts toward a position at approximately one fourth of the magnetization cycle period when a negative bias field $H_s$ is applied as illustrated in FIG. 1b.

Turning to FIG. 1c, the time of the maximum Barkhausen activity is illustrated by numeral 24 during the positive portion of the cycle which is also illustrated by time 24 in the hysteresis loop curve 26. The maximum Barkhausen activity for the negative portion of the triangular shaped wave form 10 is illustrated by time 28 in the triangular shaped wave form 10 and hysteresis loop curve 26. During the period of positive static bias field $H_s$ as illustrated in FIG. 1c, the applied magnetic field H shifts toward a position at approximately three fourths of the period when a positive bias field $H_s$ is applied.

If the static bias field $H_s$ is added to the cyclic magnetic field created by the triangular shaped wave form 10 and $H_s$, varies through the thickness of the specimen 30, the regions of the specimen at different depths will generate Barkhausen noise at different times during the magnetization cycle as illustrated in FIG. 1. This is because the applied magnetic fields H at different depths will cross zero at different times. A spatially-varying bias field can be established by two magnetic circuits as illustrated in FIG. 2. Magnet 32 is placed on the top 38 of specimen 30 and magnet 34 is placed on the bottom 39 of the specimen 30. Through the coil 36 of magnet 32, a magnetic field of $$H_A(t)=h(t)-H_o$$

is provided and applied to the top 38 of the speciment 30. Through magnet 34 and coil 40 a magnetic field of $$H_B(t)=h(t)+H_o$$

is applied to the bottom 39 of the specimen 30 where h(t) is a triangular shaped, cyclic magnetic field such as triangular shaped wave form 10; and $H_o$ is a static magnetic field. The resulting static bias field $H_S$ is created in the interior of the speciment 30 between the magnets 32 and 34. Assuming that the cyclic field h(t) is uniform throughout the specimen thickness, the combined field H of h(t) and $H_S$ at depth D into specimen 30 would cross zero at a specific time. This results in the generation of Barkhausen noise shortly after this and is illustrated by the magnetization wave forms 42, 44, and 46 at the three discrete depths $d_1$, $d_2$, and $d_3$, respectively, in the speciment 30 as illustrated in FIG. 2. Other zero crossing exists for other intermediate depths.

The zero crossing for the cyclic magnetic field H for depths from zero to $d_2$ are distributed over the top half of the magnetization wave form resulting in the Barkhausen noise occurring over an interval from approximately $t_1$ to $t_2$. Likewise, the Barkhausen noise from depths $d_2$ to $d_3$ occur over the interval $t_2$ to $t_3$. If a stress measurement is desired at a specific depth D and the time at which the magnetic field H at that depth crosses zero can be determined, then the Barkhausen noise signal can be gated during that time period and the stress at the depth D determined from the gated signal amplitude.

A. Calculations

The inventor did calculations to determine if the magnetic conditions as described in conjunction with FIG. 2 were indeed achieved. In these calculations, the applied magnetic field H produced from magnets 32 and 34 were assumed to have a triangular shape with negative and positive static bias fields as shown in FIG. 3a. The field distribution is calculated based upon the initial magnetization curve rather than the entire hysteresis loop curves 12, 20, or 26 illustrated in FIG. 1. However, the calculations provide the quantitative behavior of the magnetic field distribution under cyclic magnetization.

Figure 3B:
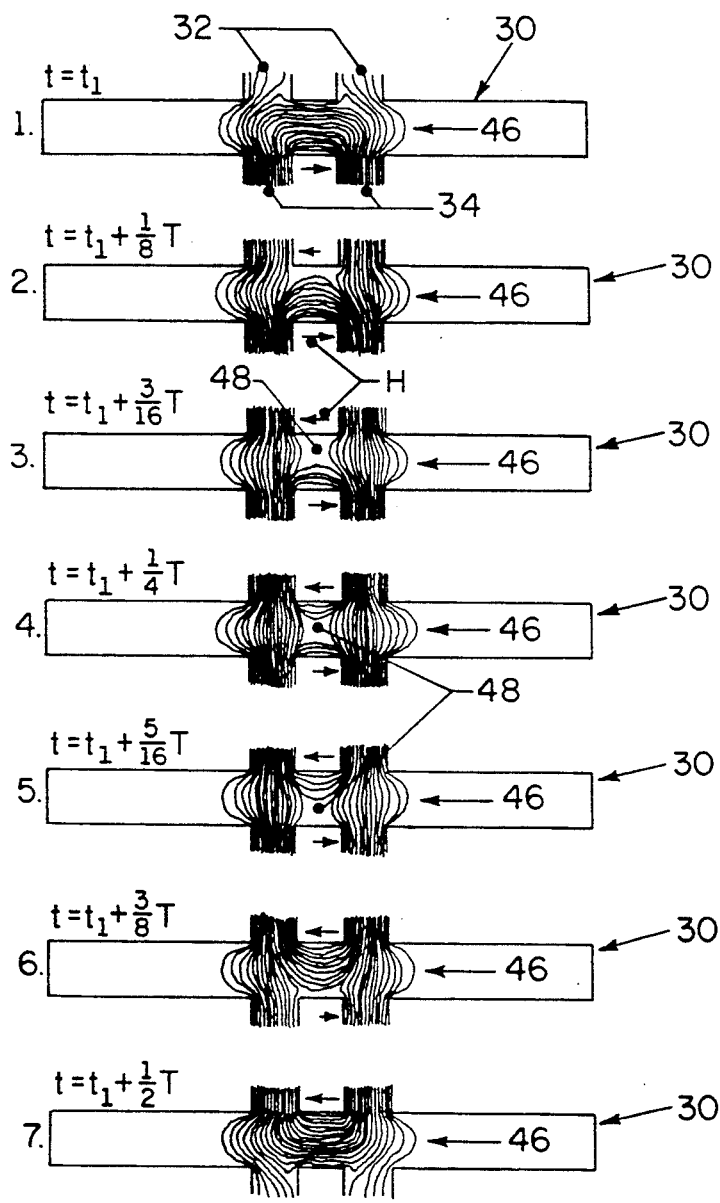

Referring to FIG. 3a, the time T is the time interval for one complete magnetization cycle with the field being applied by magnet 34 being represented by wave form 42 and the field being applied by magnet 32 being represented by wave form 44 for a total magnetic field H. The magnetic field H for seven different values of time during one half of the magnetization cycle (indicated in FIG. 3a) was calculated with the results being shown in FIG. 3b. The direction and relative magnitude of the magnetic field H produced by each magnet at each value of time t is shown by arrows as illustrated in FIG. 3b. The distribution of the magnetic field through the specimen 30 is illustrated by the wavey lines 46. Where the wavey lines 46 are further apart, the magnetic field H is lower, and where the wavey lines 46 are closer together, the magnetic field H is higher. The region where the magnetic field H crosses zero is indicated by a dot indicated with reference numeral 48 and moves across the specimen 30 as the magnetization cycle progresses. Therefore, according to the calculations as illustrated in FIG. 3b, it is possible to achieve the magnetic field conditions required to produce Barkhausen noise in different depths of the specimen at different times in the magnetization cycle.

B. Experiment Verifying Calculations

Figure 4:
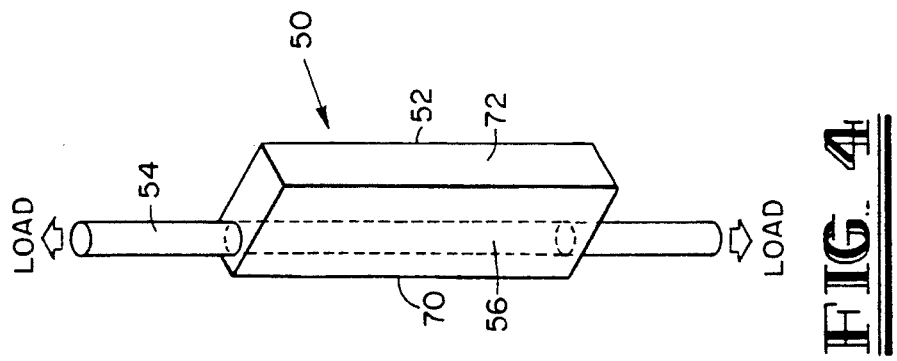
FIG. 4 is a perspective view of a specimen checked utilizing the present invention.

To verify the calculations, the inventor used two specimens in an experimental arrangement. FIG. 4 shows specimen 50 that consists of a rectangular block 52 and an internal rod 54 extending through a hole 56 drilled through the rectangular block 52. There should be a tight relationship between the internal rod 54 and the hole 56 with a light oil being applied to the rod 54 before insertion in the hole 56 to improve the acoustical coupling and reduce friction between the internal rod 54 and the rectangular block 52. The specimen 50 was designed so that a localized subsurface stress could be produced in one region while the remainder of the specimen 50 was unstressed. This allows specimen 50 to show that the Barkhausen noise occurring in the localized stressed region could be distinguished from that occurring in the unstressed region.

While the construction of the specimen 50 may be of any particular design, the configuration shown in FIG. 4 uses a 4.76 millimeter diameter rod 54 inserted in hole 56 and the rectangular block 52 having dimensions of 5.08 centimeters $\times 1.60$ centimeter $\times 0.64$ centimeters. Both the internal rod 54 and the block 52 are fabricated from AISI 4340 steel in the normalized and tempered condition. The relatively tight fit between rod 54 and the rectangular block 52 provide a good acoustical and magnetic coupling, yet allow the rod to slide in the block. A localized tensile stress in only the rod portion of the specimen can be produced by the application of a tensile load on both ends of the rod 54 as illustrated in FIG. 4. A strain gauge can be bonded to the rod 54 to determine the magnitude of the applied stress or load.

For comparison, another specimen (not shown) was used to obtain the acoustical Barkhausen response as a function of uniform (no localized) stress. This specimen consisted of a 40 centimeter $\times 1.60$ centimeter $\times 0.64$ centimeter rectangular block of normalized and tempered AISI 4340 steel which was loaded in uniaxial tension. This was for purposes of comparison with the specimen 50 in the stressed condition.

Figure 5:
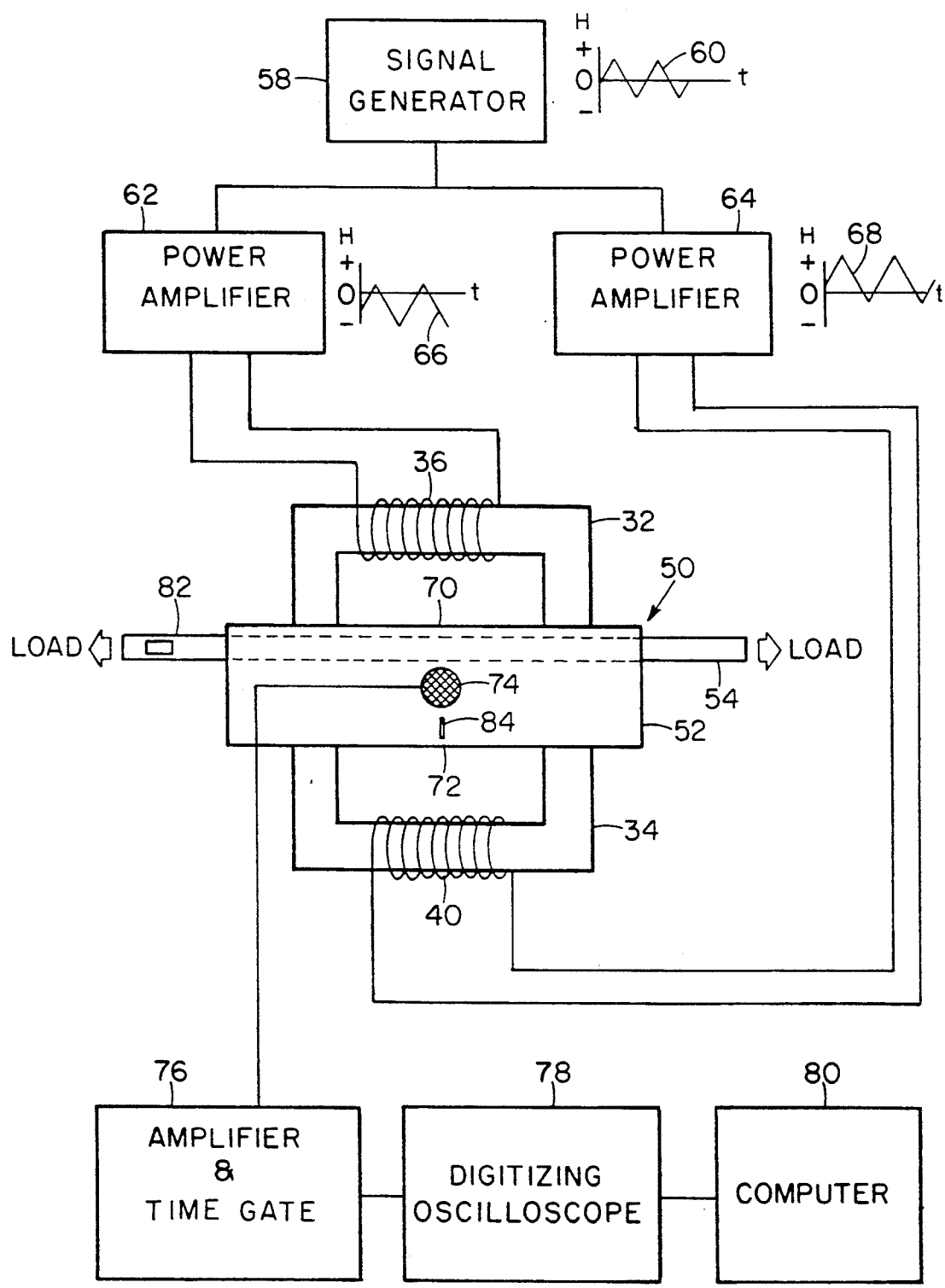
FIG. 5 is an illustrated block diagram of the present invention used to determine stress in the specimen illustrated in FIG. 4.

Referring to FIG. 5, a schematic block diagram is shown for checking the internal stress on specimen 50 as described hereinabove. To produce a spatially-varying bias field, the arrangement with magnets 32 and 34 and their respective coils 36 and 40 is shown as previously described in connection with FIG. 2. A signal generator 58 provides a triangular shaped magnetization current wave form 60 as illustrated in FIG. 5 to power amplifiers 62 and 64. The power amplifiers 62 and 64 provide opposing triangular shaped magnetizing current wave forms 66 and 68, respectively, as shown in FIG. 5 to their respective coils 36 and 40. The frequency of the wave forms 60, 66 and 68 is one hertz (Hz). Internally within the power amplifiers 62 and 64, the static bias magnetic fields are added to the triangular wave forms 66 and 68.

By applying the wave form 66 and 68 to face 70 and 72 via the magnets 32 and 34, respectively, Barkhausen signals are created in specimen 50. The Barkhausen signals are detected by a wide band acoustic transducer 74 which has a relatively flat frequency response from 75 kilohertz to 450 kilohertz (kHz). The transducer 74 may be held in place by any of a number of means such as vacuum grease or a clamp. The signals from the acoustic transducer 74 are fed to an amplifier and timegate 76. The amplifier portion has low noise and the time-gate portion provides an analog signal proportional to the amplitude of an acoustical noise such that a particular piece of information is identified from the true stream of data burst. The analog signal is fed to digitizing oscilloscope 78 which averages signals from successive magnetization cycles to enhance the signal to noise ratio of the detected time gate signals. From the digitizing oscilloscope 78, the signal is fed to a computer 80. From the computer 80, the information is used by the computer's record to plot the Barkhausen activity. The Barkhausen activity which is proportional to stress is then used to prepare a tomographic map indicating the internal stress within the specimen 50.

To determine the load being applied to the rod 54, a strain gauge 82 is located on rod 54. This simply provides a redundant check to insure the proper load is being applied to rod 54. Also, hall effect sensor 84 provides a redundant check on the Barkhausen effect detected by the acoustical transducer 74.

C. Experimental Results

Figure 6:
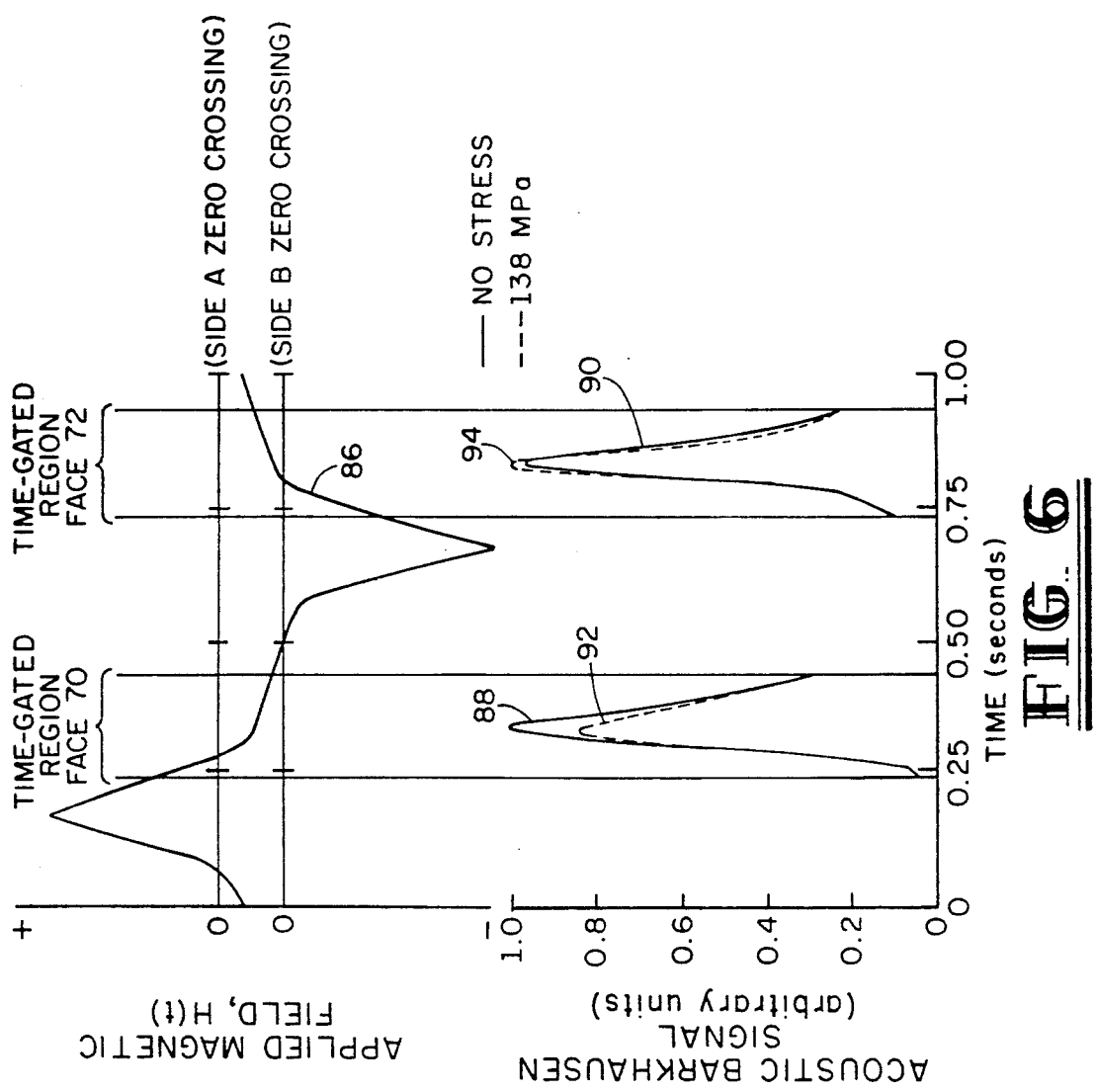
FIG. 6 is the magnetic field wave forms and time-gated acoustical Barkhausen signals from both sides of the specimen illustrated in FIG. 4 as checked by the configuration shown in FIG. 5, with and without stress applied to an internal rod.

Referring now to FIG. 6, a typical example of the applied magnetic field wave form H(t) as measured in speciment 50 with the hall effect sensor 84 being near face 70 (close to the rod 54) is shown. The zero level of the field measured at side 70 is shifted in the positive direction due to the negative static field (minus $H_s$). The zero level for face 72 is also shown in FIG. 6 and is shifted in a negative direction due to the positive static field ($H_s$) on face 72 of the specimen 50. The measured magnetic field wave form 86 show a spatially-varying bias field with a superimposed cycling field and proves applicant's invention.

The ideal spatially-varying bias field as illustrated in FIG. 2 would have produced zero crossing levels of the magnetic field H(t) which were approximately equal to the peak amplitude of the cyclic field on each edge of the specimen 50. If the ideal had been achieved, it would have resulted in zero crossing levels (and thus the Barkhausen noise) for different depths in the specimen 50 being distributed over approximately the entire magnetization cycle as illustrated in FIG. 2. However, as experimentally shown in FIG. 6, the desired static bias field levels near the edges of the specimen 50 could not be achieved with the experimental arrangement illustrating applicant's invention.

In addition, the shape of the cycling magnetic field H(t) was not triangular, but distorted as shown in FIG. 6. Because of this less than ideal applied magnetic field conditions, the zero crossings of the magnetic fields for positions from about the center line of the specimen 50 to the edge of the specimen occurred in a relatively short period of time t. As a result, the detected acoustic Barkhausen noise was concentrated in a relatively narrow, distinct peaks instead of being spread over the entire magnetization cycle.

The acoustical Barkhausen signal obtained from specimen 50 is illustrated in the bottom portion of FIG. 6. The acoustical signal has been time-gated to show only one of two peaks from each side of the specimen 50. Each peak follows a zero crossing of the field on each side of the speciment 50, and therefore, the peaks are associated with the respective faces 70 and 72 of the specimen 50 as designated in FIG. 4.

Since the zero crossing of the field H occurred over a relatively short period of time for positions from each face 70 or 72 of the specimen 50 to the center, the Barkhausen activity produced in approximately one half of the specimen 50 (from approximately the center line to one face 70 or 72) is concentrated in each peak. Because the Barkhausen activity occurred in a relatively narrow region instead of being spread over the magnetization cycle, it is difficult to time-gate specific regions of the signal to isolate the Barkhausen response at precise depths. However, the spatial resolution was effectively limited to distinguishing Barkhausen activity produced in one half of the specimen 50 from Barkhausen activity produced in the other half of the specimen 50. Even though the spatial resolution obtained needs considerable improvement, the results shown in FIG. 6 confirm that it is possible to make different regions of the specimen 50 generate Barkhausen noise at different times of the magnetization cycle.

To verify that stresses at different depths in the specimen 50 could be determined by measuring acoustical Barkhausen noise produced at different times in the magnetization cycle, acoustic Barkhausen signals are measured with and without tensile load supplied to rod 54 of the specimen 50. The effect of applied stress to the rod 50 (with the remainder of the specimen unstressed) is shown at the bottom of FIG. 6. The peaks represented by the solid lines 88 and 90 represent no stress, while the peaks represented by broken lines 92 and 94 indicate the acoustic Barkhausen signal when a 138 MPa tensile stress is applied to rod 54 of the specimen 50. The peaks 90 and 94 of face 72 of the specimen 50 (opposite from the rod 54) is essentially insensitive to the stress and shows little change. The effect of the stress is quite apparent, however, in the peaks 88 and 92 from face 70 (where the rod 54 is located). The 15 percent decrease observed in the amplitude of peaks 88 and 92 results from the rod being stressed. This indicates localized subsurface stress produced by the rod 54 can be distinguished from the unstressed region of the specimen 50.

Figure 7:
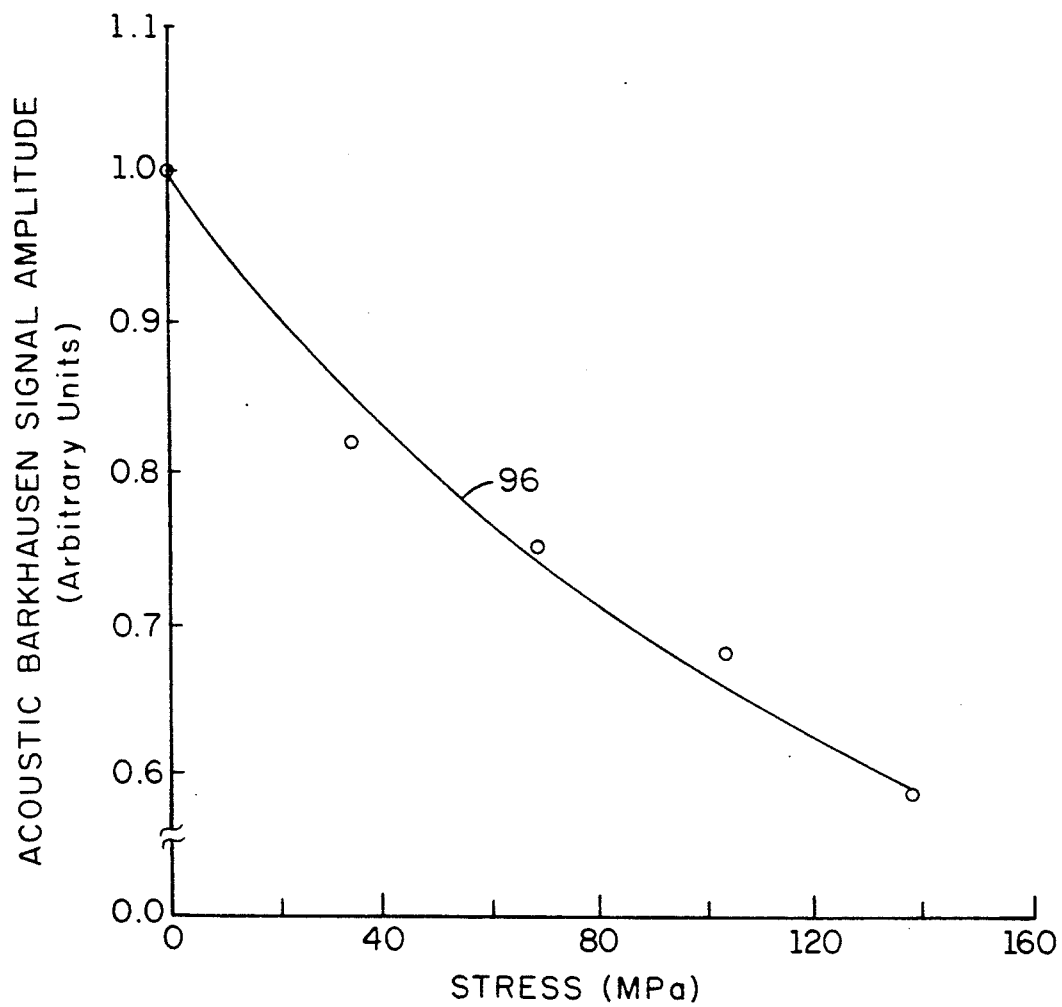
FIG. 7 is a chart of the acoustical Barkhausen signal amplitude versus an applied uniform uniaxial stress to the specimen.

The observed acoustical Barkhausen signal amplitude change with stress applied to rod 54 can be compared with the acoustical Barkhausen signal amplitude obtained as a function of uniform, uniaxial stress from the other specimen (not shown). The data for uniform stress is shown in FIG. 7. The curve 96 of FIG. 7 illustrates the acoustical Barkhausen signal decreases 42 percent with the application of 138 MPa tensile stress. This compares with the 15 percent decrease in signal amplitude from specimen 50 with a 138 MPa tensile stress applied to the internal rod 54.

The observed 15 percent decrease in signal amplitude between peaks 88 and 92 of FIG. 6 can be explained as follows. Barkhausen noise pulses generated at different regions in the material are expected to have a random distribution of amplitude, phases and frequencies and are, therefore, incoherent. Thus, the overall effective amplitude of the Barkhausen noise signal A can be expressed as follows.

$$A = a_i^2 v_i / v_i^{\frac{1}{2}}$$

where
   $a_i$ is the amplitude of the noise generated from the $i^{th}$ noise source of volume $v_i$. The Barkhausen signal obtained from the half of the specimen 50 containing rod 54 can be considered as consisting of noise signals from two sources; the rod 54 and the remaining half of the specimen 50. Assuming that the signals from the rod 54 decrease by 42 percent with 138 MPa stress and the signal from the remainder of the specimen 50 does not change, then addition of the signals as described above results in a combined signal which decreases by 13 percent. A calculated 13 percent change agrees well with the observed 15 percent change. This supports the previous conclusion that the peaks 88 and 92 from side A represent Barkhausen noise generated from the half of the specimen 50 near face 70.

Barkhausen noise can be produced in specific interior regions of a ferromagnetic specimens at different times than the magnetization cycle by applying a combination of cycling and spatially-varying bias magnetic fields as described hereinabove. By time-gating the acoustically detected Barkhausen signals, the stress in a specific region can be determined from the signal amplitude. Test results from a specimen in which a localized subsurface stress was produced substantiated the approach. This method of determining stress using a combination of cycling and spatially-varying bias magnetic fields is then used for tomographic mapping of stress distribution in the interior regions of a ferromagnetic specimen.

I claim:
1. An apparatus for non-destructive testing utilizing Barkhausen noise to determine stress at depths within an unknown ferromagnetic material by comparing to a known ferromagnetic material at a similar depth, said apparatus comprising:
   means for generating a cyclic time varying magnetic field within said unknown ferromagnetic material;
   means for maintaining a constant magnetic field gradient from a first side of said unknown ferromagnetic material to a second side of said unknown ferromagnetic material, said constant magnetic field gradient in combination with said time varying magnetic field producing a singular element within said unknown ferromagnetic material with a net zero magnetic field, said singular element varying in position over time within said unknown ferromagnetic material, said Barkhausen noise occurring when said singular element passes through said depths within said ferromagnetic material;
   detecting means adjacent said unknown ferromagnetic material, said detecting means receiving said

Barkhausen noise and generating a detected signal proportional thereto;

means for receiving said detected signal from said detecting means and selecting a portion of said detected signal that represents said Barkhausen noise from said unknown ferromagnetic material emitted at a predetermined time in a cycle of said cyclic time varying magnetic field and thereby to be known to have occurred at a given depth of said depths within said unknown material;

means for comparing said Barkhausen noise at said predetermined time in said unknown ferromagnetic material with Barkhausen noise from said known ferromagnetic material at said given depth to determine if stress exists in said unknown ferromagnetic material at said given depth.

2. The apparatus for utilizing Barkhausen noise to determine stress at depths within said unknown ferromagnetic material as recited in claim 1 further comprising means for moving said said time varying magnetic field and said constant magnetic field gradient from a first location within said unknown material to other locations, information concerning stress being stored in computer means at said known, but varying, depths at each location indicating stress within said unknown ferromagnetic material.

3. The apparatus for utilizing Barkhausen noise to determine stress at depths within said unknown ferromagnetic material as recited in claim 2 further including recording means for receiving said information from data processing part of said computer generating a tomographic map of stress within said unknown ferromagnetic material.

4. An apparatus for non-destructive testing utilizing Barkhausen noise to determine stress at depths within an unknown ferromagnetic material by comparing to a known ferromagnetic material at a similar depth, said apparatus comprising:

signal generator means for generating a combined cyclic magnetic field signal and spatially-varying magnetic field signal;

first electromagnet having first coil means for receiving said combined cyclic magnetic field signal and spatially-varying magnetic field signal;

second electromagnet having second coil means for receiving said combined cyclic magnetic field signal and spatially-varying magnetic field signal, said first electromagnet and said second electromagnet being positioned at a first location on opposing sides of said unknown ferromagnetic material to create a cyclic magnetic field and a spatially-varying magnetic field therein where said depths of said unknown ferromagnetic material passes through a zero magnetic field to create said Barkhausen noise;

detecting means adjacent said unknown ferromagnetic material and near said first and second electromagnets, said detecting means receiving said Barkhausen noise and generating a detected signal proportional thereto;

gate means for receiving said detected signal from said detecting means which represents said Barkhausen noise from said unknown ferromagnetic material at a predetermined time in a cycle of said cyclic magnetic field so that said Barkhausen noise at said predetermined time is at a given depth of said depths;

comparing means for utilizing said Barkhausen noise at said predetermined time in said unknown ferromagnetic material and comparing with Barkhausen noise from said known ferromagnetic material at said given depth.

first and second amplifier between said signal generator means and said first and second coil means, respectively, said first amplifier adding a negative static magnetic field signal to said cyclic magnetic field signal and said second amplifier adding a positive static magnetic field signal to said cyclic magnetic field signal to create said spatially-varying magnetic field signal.

5. The apparatus for utilizing Barkhausen noise to determine stress at depths within said unknown ferromagnetic material as recited in claim 1 wherein said detecting means includes an acoustic transducer for receiving said Barkhausen noise, said apparatus further comprising:

acoustical amplifier for increasing acoustic signals from said acoustic transducer;

said gate means being connected to said acoustical amplifier for setting said predetermined time.

6. A method for non-destructive testing of an unknown ferromagnetic specimen for stress at any depth therein using Barkhausen noise, said method including the following steps:

generating a cyclic magnetic field signal by a signal generator;

adding a negative magnetic field signal to said cyclic magnetic field signal and a positive magnetic field signal to said cyclic magnetic field signal;

magnetizing said unknown ferromagnetic specimen at a given location with first and second electromagnets on opposing faces thereof, a first coil of said first electromagnet receiving said negative magnetic field signal and said cyclic magnetic field signal and a second coil of said second electromagnet receiving said positive magnetic field signal and said cyclic magnetic field signal to create at said given location a cyclic and spatially-varying magnetic field within said unknown ferromagnetic specimen;

sensing Barkhausen noise at said given location by a detector near said first and second electromagnets and adjacent a surface of said unknown ferromagnetic specimen;

gating said Barkhausen noise from said detector by an electrical gate to coincide with a first time during a cycle of said cyclic magnetic field thereby giving Barkhausen noise at a first depth of said unknown specimen; and computing stress at said first depth by a computer based on said Barkhausen noise received from said electrical gate.

7. The method for non-destructive testing of an unknown ferromagnetic specimen as recited in claim 6 for stress at any depth therein using Barkhausen noise including repeating the steps to give Barkhausen noise at other depths in said unknown ferromagnetic specimen and hence stress at said other depths.

8. The method for non-destructive testing of an unknown ferromagnetic specimen as recited in claim 7 for stress at any depth therein using Barkhausen noise including the steps of relocating said first and second electromagnets and repeating prior steps to indicate stress within said unknown ferromagnetic specimen at different locations and depths.

9. The method for non-destructive testing of an unknown ferromagnetic specimen as recited in claim 8 for stress at any depth therein using Barkhausen noise including a final step of producing a tomograph map of stress within said unknown ferromagnetic specimen by said computer.

* * * * *